(12) United States Patent
Vogtmeier et al.

(10) Patent No.: US 7,465,931 B2
(45) Date of Patent: Dec. 16, 2008

(54) RADIATION DETECTOR MODULE

(75) Inventors: Gereon Vogtmeier, Aachen (DE); Ralf Dorscheid, Kerkrade (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 21 days.

(21) Appl. No.: 10/596,026

(22) PCT Filed: Nov. 19, 2004

(86) PCT No.: PCT/IB2004/052490

§ 371 (c)(1),
(2), (4) Date: Mar. 7, 2007

(87) PCT Pub. No.: WO2005/052636

PCT Pub. Date: Jun. 9, 2005

(65) Prior Publication Data

US 2007/0242804 A1    Oct. 18, 2007

(30) Foreign Application Priority Data

Nov. 28, 2003  (EP) ................................ 03104461

(51) Int. Cl.
*G01T 1/24* (2006.01)
(52) U.S. Cl. .................... 250/370.09; 378/19
(58) Field of Classification Search ............... 250/394, 250/370.09
See application file for complete search history.

(56) References Cited

U.S. PATENT DOCUMENTS

| | | | |
|---|---|---|---|
| 4,405,863 A | 9/1983 | Pritzkow et al. | |
| 4,521,689 A * | 6/1985 | Pritzkow | 250/385.1 |
| 4,543,490 A | 9/1985 | Gupta | |
| 4,709,382 A | 11/1987 | Sones | |
| 5,487,098 A * | 1/1996 | Dobbs et al. | 378/19 |
| 5,629,524 A | 5/1997 | Stettner et al. | |
| 5,668,851 A | 9/1997 | Dobbs | |
| 5,991,357 A | 11/1999 | Marcovici et al. | |
| 6,396,898 B1 * | 5/2002 | Saito et al. | 378/19 |
| 6,510,195 B1 | 1/2003 | Chappo et al. | |
| 6,587,538 B2 * | 7/2003 | Igarashi et al. | 378/19 |
| 6,982,423 B2 | 1/2006 | Elgali | |
| 2002/0130266 A1 * | 9/2002 | Kyyhkynen | 250/370.09 |
| 2004/0065465 A1 * | 4/2004 | Chappo et al. | 174/66 |

FOREIGN PATENT DOCUMENTS

EP    0 109 204 A2    5/1984

* cited by examiner

*Primary Examiner*—David P Porta
*Assistant Examiner*—Jessica L Eley

(57) ABSTRACT

The present invention relates to a detector, in which detector modules are two-dimensionally arranged. The problem of the two-dimensional arrangement of detector modules is solved by a base structure (1) with guide elements (2) on which the detectors modules (3) with at least one respective guide structure (4), are positioned relative to at least one of the respective guide elements, the guide elements (2) extending in a first direction (R1), at least two of the detector modules (3) being positioned consecutively on one of the guide elements (2) in the first direction (R1), and there are guide elements (2) that are separated from one another in a second direction (R2).

20 Claims, 5 Drawing Sheets

Figure 3:
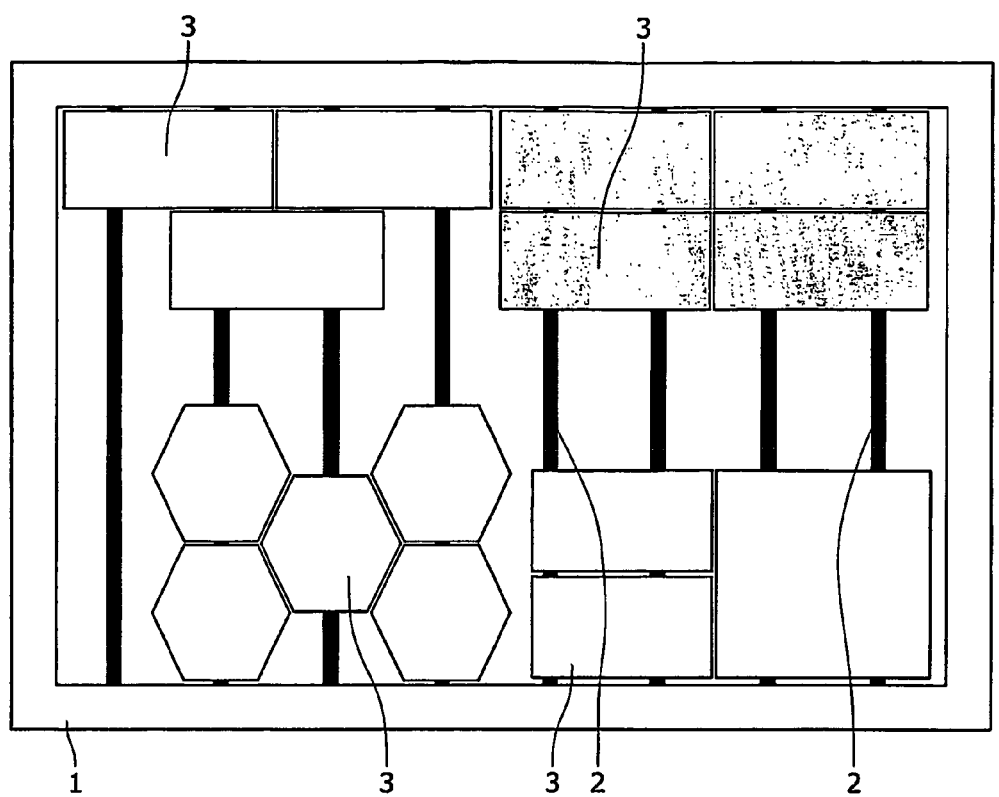

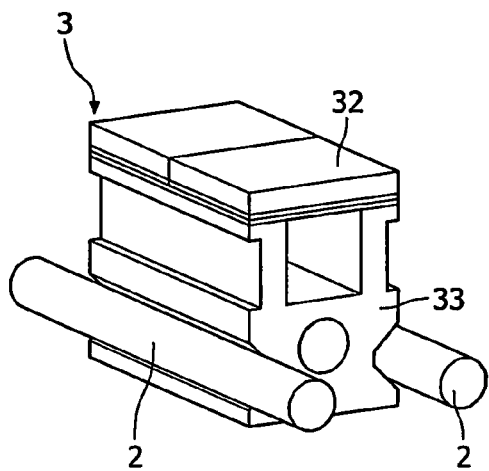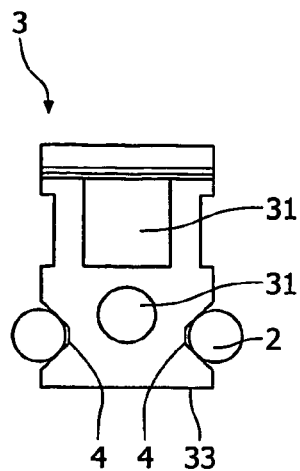
FIG.1a   FIG.1b
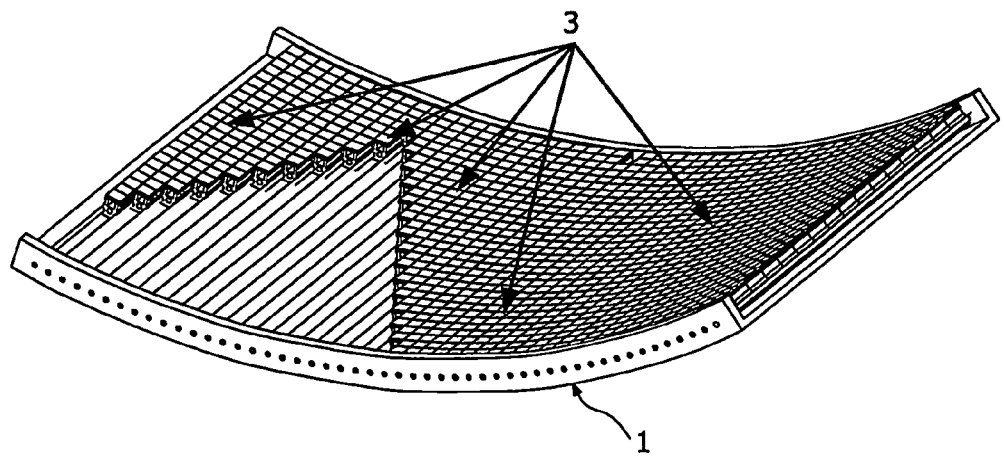
FIG.2

RADIATION DETECTOR MODULE

The invention relates to a detector, in particular an X-ray detector as is used in an imaging X-ray device.

U.S. Pat. No. 5,668,851 describes a detector which has a base element into which precision holes are drilled and that which also has alignment pins. Detector modules are positioned and fastened to the base element by means of the alignment pins.

It is an object of the invention to provide a detector, in particular an X-ray detector such as is used in an X-ray device which allows a two-dimensional arrangement of detector modules.

The object is achieved by a detector comprising
a base structure with guide elements
detector modules with at least one respective guide structure for positioning relative to at least one of the respective guide elements, wherein
the guide elements extend in a first direction,
at least two of the detector modules are positioned consecutively on one of the guide elements in the first direction and
there are guide elements which are separated from one another in a second direction.

Detectors of modern or future X-ray devices are very large. $40 \times 40$ cm$^2$ for normal transmission X-ray imaging, $60 \times 60$ cm$^2$ for nuclear medical imaging (for example by means of positron emission tomography—PET—or single photon emission computed tomography—SPECT) or $100 \times 60$ cm$^2$ for future CT detectors which, without the patient or the detector having to be moved in the direction of the longitudinal extension of the patient, allow a volume of the patient to be examined in which, for example, the entire beating heart is located, are already being used or have been thought of If large detectors of this type have been assembled from individual detector modules (as is conventional in the case of CT detectors nowadays in a one-dimensional arrangement), only a single detector module has to be replaced and not the entire detector when there is a defect in one of the detector modules. The positioning of the individual detector modules is a problem here, however. These should be arranged, as far as possible, such that the position is precisely known and that the edges of the detector modules, with the smallest possible spacing, do not collide with one another, so a substantially closed detector face can be formed. Thus, the detector modules have a sensitive surface for detecting X-ray radiation. A two-dimensional arrangement of detector modules then produces a two-dimensional, sensitive detector surface formed from the individual sensitive surfaces of the detector modules.

In a detector according to a first embodiment, there is a base structure with guide elements. The detector modules have guide structures, by means of which the detector modules can be positioned relative to the guide elements. The precision of the entire arrangement is therefore predetermined by the guide elements. Guide elements, for example guide rods, can easily be produced, for example by centerless grinding. The guide elements extend in a first direction. In this first direction of extension, detector modules can be positioned on the guide elements. There are guide elements here which are separated from one another in a second direction, so that detector modules can also be arranged in the second direction. A base structure of this type with guide elements allows two-dimensional arrangements of detector modules. In the process, the detector modules are positioned on the guide elements in the first direction and, in the second direction, guide elements with detector modules positioned thereon are arranged next to one another, so that overall an arrangement of detector modules is produced in the first direction and in the second direction and this leads to a two-dimensional arrangement In the process, the second direction between two respective guide elements does not have to remain the same, but it may change, so that the two-dimensional arrangement of detector modules is curved.

Since the guide elements extend in one direction, the detector modules can easily be positioned on these guide elements, for example by slipping on. If one of the detector modules has a defect, it can be removed comparatively easily and replaced in that, in the first direction (the extension direction), the detector modules positioned prior to the defective detector module are slipped off. Once the defective module has been replaced, the modules which were previously slipped off, are slipped on again.

In an embodiment according to the invention, according to a further embodiment, there are spacer elements which are arranged either between the base structure and one of the detector modules or between two of the detector modules on the guide elements. Spacer elements can be produced very precisely, for example by flat grinding and thus allow the precise positioning of detector modules relative to one another or relative to the base structure. When detector modules are slipped on, time-consuming and laborious checking of the positioning is unnecessary, as the spacer elements predetermine the positioning of detector modules to the base structure or to one another in the first direction.

In another embodiment according to the invention, the guide elements in the second direction are arranged with a spacing pattern with respect to one another. "Spacing pattern" means here the sequence of spacings between the guide elements (measured from center to center). A "spacing between two guide elements" is then the sum of the spacings from a first guide element up to a second guide element. If the detector modules in the second direction have an extent which substantially corresponds to one of the spacings between two of the guide elements, this allows the practically gapless arrangement of detector modules with respect to one another and a substantially continuous sensitive detector surface can be formed from the sensitive surfaces of the individual detector modules. Thus the spacing pattern between the guide elements may be a sequence of constantly equal spacings, which leads to the fact that modules always with the same configuration can be used in order to form the total sensitive detector surface. As each detector module can be configured to be the same, a reduction in production costs is also produced.

In a further embodiment according to the invention, the base structure in one direction, which is not the first direction, is curved. Curved detector surfaces can also be formed in this way without giving up the easy producibility of the guide elements which extend in the first direction. In the case of a curve, it means that the second direction follows the curve between two respective adjacent guide elements. The detector modules can still all be configured the same when the curve is constant.

In a further embodiment according to the invention, two detector modules have a different shape. A different shape also means the same shape with different dimensioning. Thus a square detector module can be used on one part of the detector, for example, instead of a 2×2 arrangement of detector modules of half the size. However, any other divisions of the total detector face into individual surfaces of the detector modules are conceivable.

In another embodiment according to the invention, the guide elements are rods. Rods can be easily and precisely produced, for example by centerless grinding.

In an embodiment according to the invention which is different again, there is at least one clamping element which is provided for fixing a detector module with respect to the guide element on which it is positioned. Clamping elements allow detector modules to be fixed, so that despite easy displaceability of the detector modules in a maintenance or production state, the detector modules are fixed in an operating state.

In a further embodiment according to the invention, the detector modules each have at least one continuous recess in the first direction. Recesses, in particular continuous cavities and indentations, are used to accommodate electronic components and can offer space for the current supply and data and signal lines, so that easy accessibility is provided for the respective electronics of a module and the necessary lines can be accommodated in a two-dimensional detector arrangement. This is made possible, in particular in that the continuous recesses are introduced into the detector modules in such a way that continuity is achieved over the entire detector, for example in the first direction, so that data lines and power supplies can be guided through the recesses of consecutively arranged detector modules.

The invention also relates to an X-ray device in which a detector according to the invention is used.

The invention also relates to a method for producing a detector according to the invention.

Figure 4:
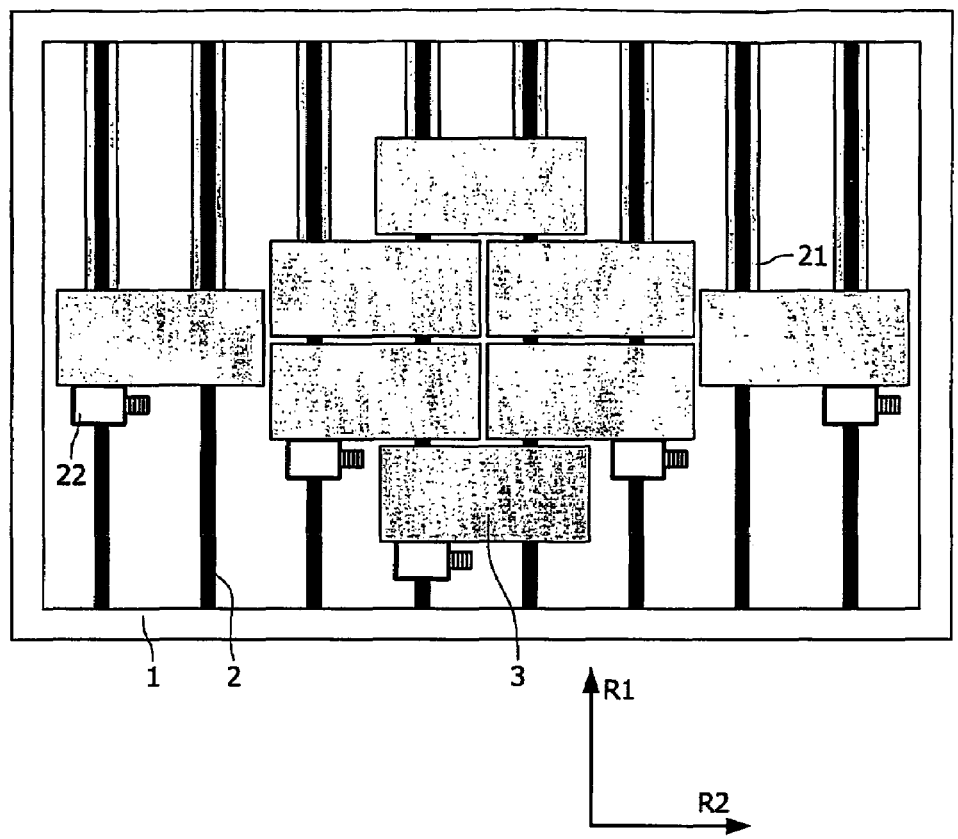
Figure 5:
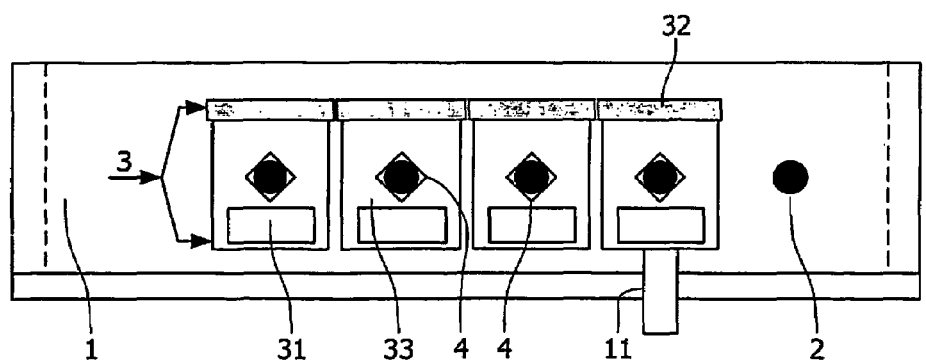
Figure 6:
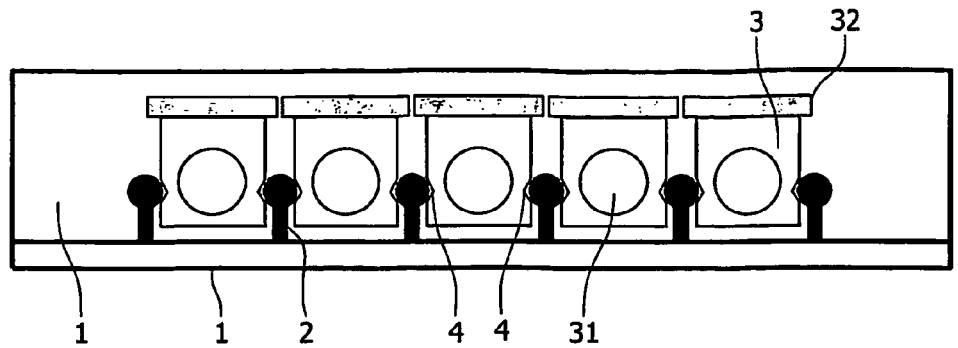
Figure 7:
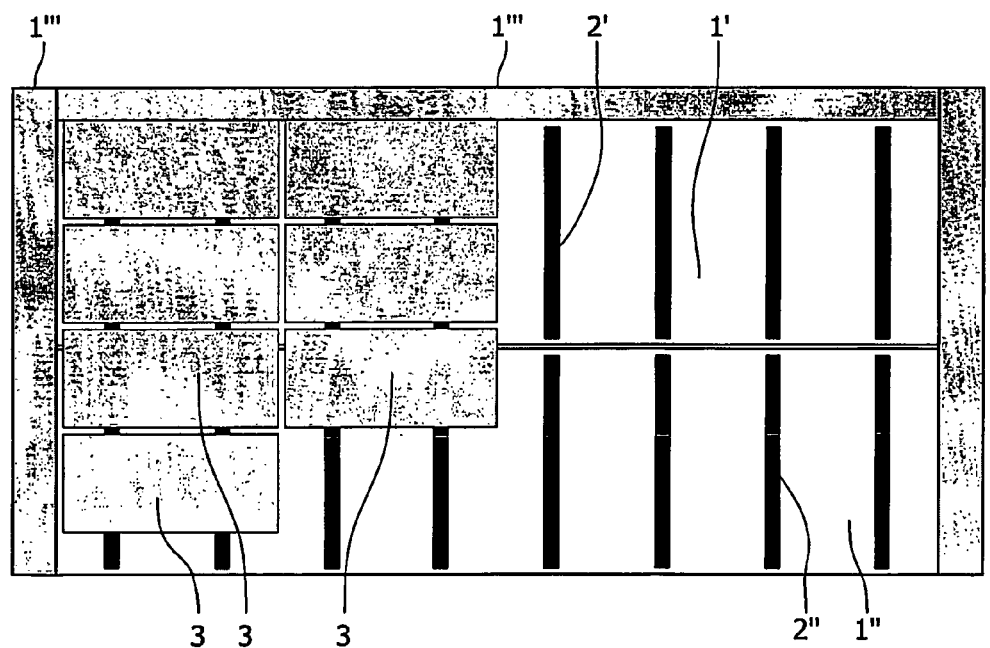
Figure 8:
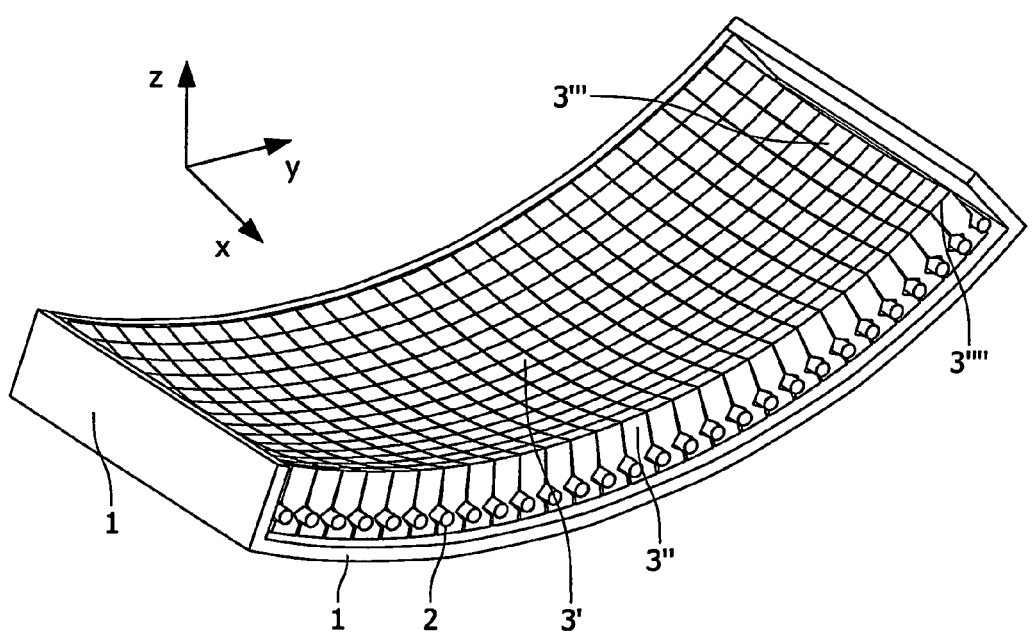

The invention will be described in detail hereinafter by drawings and a plurality of embodiments. In the drawings:

FIG. 1a shows a detector module by way of example, which detector module is positioned by means of two guide structures on two guide elements (only shown in cut-away form), FIG. 1b shows the detector module from FIG. 1a in a front view, in other words in the viewing direction of the extension direction of the guide elements, FIG. 2 shows a detector according to the invention with a base structure, guide elements and two-dimensionally arranged detector modules, FIG. 3 shows a base structure with guide elements and, by way of example, four arrangements of detector modules, in plan view, FIG. 4 shows a base structure with guide elements and an arrangement of detector modules, by way of example, spacer elements being used for positioning of the detector modules and clamping elements being used for fixing, FIG. 5 shows a lateral view of a base structure with guide elements and arranged detector modules, FIG. 6 shows a lateral view of a detector as in FIG. 5, but with a different embodiment of guide elements and guide structures, FIG. 7 shows a base structure consisting of a plurality of parts, so that the detector is easily scalable, and FIG. 8 shows a detector according to the invention with a base structure, guide elements and detector modules which are each differently formed in such a way that the total detector surface forms a cut-out from a conical face.

FIG. 1a shows, by way of example, a detector module 3, as it is arranged in a detector according to the invention. The detector module 3 has a sensitive surface 32 which may be, for example, a scintillator layer with photodiodes located below it for detecting X-ray quantums or a directly converting material. The remaining part of the detector module 3 is the base body 33 of the detector module 3. The detector module 3 is positioned on two guide elements 2 which are shown here in cut-away manner and are to be imagined fastened at their ends to a base structure. It can be seen from FIG. 1a that further detector modules can be arranged consecutively in the direction of extension (in other words in the direction of the longitudinal axis) of the guide elements prior to and after the detector module shown on the same guide elements. FIG. 1b shows a front view of the detector module 3, by way of example, from FIG. 1a, with the viewing direction in the direction of extension of the guide elements. In this embodiment, the detector module 3 has two guide structures 4 which closely abut the guide elements 2 which in this embodiment are guide rods, substantially without mechanical play. Guide elements 3 and guide structures 4 therefore act by means of a pointwise or flat mutual abutment without substantial mechanical play with one another and thus produce the precise positioning ability and displaceability of the detector modules. Both guide rods, which in this example have a round cross-section, and the trapezoidally recessed guide structures 4 can be produced easily, economically and above all with great precision. It emerges from FIG. 1b that further detector modules can easily be arranged laterally next to the detector module 3 shown. The detector module shown then shares, in the embodiment shown, one of the respective guide elements 2 with a respective lateral neighbor (reference is made here to FIG. 6, where this type of arrangement is shown for a different embodiment of the guide elements). In total, the fact that a large number of guide elements, which are fastened, for example, by means of precision holes in a base structure (see FIG. 2 in this regard), enable detector modules to be precisely two-dimensionally arranged. The more precisely the various components of the detector are manufactured, the more precise is the positioning. If the guide elements are configured as guide rods, these can be manufactured, for example, by centerless grinding at lengths up to 600 mm with a precision of <2 µm with respect to concentricity and diameter and <5 µm with respect to straightness. Aluminum or steel can be used, for example, as the material. Special iron alloys (such as, for example, the alloy known by the commercial name Invar), which only have a very low coefficient of thermal expansion, can also be used. The base bodies 33 of the detector modules 3 can be produced, for example, by means of CNC milling or wire-EDM, in which tolerances of a few µm (≈5 µm for positional tolerance and ≈3 µm for geometrical tolerance) are achieved. The sensitive surface 32 of a detector module 3 is typically applied later, for example by adhesive bonding.

FIG. 2 shows a detector according to the invention in which a large number of detector modules 3 according to FIGS. 1a and 1b are two-dimensionally arranged. The individual detector modules are, as in FIGS. 1a and 1b, each arranged on two respective guide elements. The guide elements are only indicated in this view. The guide rods are to be thought of as fastened in the base structure 1; The base structure in the embodiment shown consists of a cylindrically curved base part and two side parts. In the leading side part, precision holes can be seen, in which the guide rods are fastened. Precision holes can be produced by jig milling with a position tolerance of about 3 µm and a geometrical tolerance of about 2 µm. In this instance, the material of the base structure 1 can be selected so as to be the same as the material of the guide elements 2 and the base bodies 33 of the detector modules 3, so temperature expansions do not cause a tolerance problem. The base structure 1 is used to stabilize the whole arrangement. If the detector elements have a sensitive surface of 2×4 cm$^2$, the detector shown with a two-dimensional detector module arrangement of 50×16 detector modules then has a sensitive detector face of 100×64 cm$^2$ and this is a typical size for a CT detector for recording the human heart or liver. The two-dimensional arrangement of detector modules 3 is achieved in that the detector modules 3 are each slipped onto guide elements 2 and displaced in the first direction (the extension direction of the guide elements 2) until they have achieved a predetermined position. The guide elements 2 are, in each case, arranged offset with respect to one another in a second direction (the guide elements 2 in the embodiment shown are located on a cylinder surface section). By slipping detector modules 3 consecutively onto guide elements 2 arranged in an offset manner, a two-dimensional arrangement of detector modules 3 is achieved overall.

FIG. 3 shows a plan view of a detector according to the invention, in which four two-dimensional detector module arrangements are shown by way of example. The base structure 1, which in this example is configured as a rectangular from, is used for stabilizing the whole arrangement. Guide elements 2 are connected to the base structure 1, for example in that the guide elements 2 are let into precision holes in sides of the base structure 1 and are optionally screwed in there. As shown in FIGS. 1a and 1b, the detector modules 3 are arranged on the guide rods 2 by means of guide structures. Four two-dimensional detector arrangements are shown by way of example at top left, top right, bottom left and bottom right in the drawing. Four rectangular detector modules are arranged at top right in a rectangular 2×2 matrix. Three rectangular detector modules are arranged at top left in a 2×1 matrix which is offset by half the longitudinal extent. Five hexagonal detector modules are arranged in a two-dimensional, hexagonal matrix at bottom left. Arranged at bottom right, are three rectangular detector modules 3, with the right-hand one of the three detector modules being larger than the two other detector modules and thus having the size of a 2×2 arrangement of the smaller detector modules.

FIG. 4 shows a further detector according to the invention with a base structure 1 (which is a rectangular flame here), detector modules 3 and guide elements 2. A two-dimensional arrangement of detector modules 3 covers a large area in the center and the detector face tapers at the sides, so that a non-rectangular overall detector face is produced. The extension direction of the guide elements (the first direction) is indicated by an arrow R1. The second direction, in which the guide elements are arranged separate from one another, is indicated by an arrow R2. In the embodiment according to FIG. 4, the second direction R2 is spatially constant and is therefore applicable to each pair of guide elements. In general, the direction R2 is only defined, however, between two respective guide elements. To ensure precise positioning relative to the base structure 1, spacer elements 21 are used which are thus slipped onto the guide elements 2 between the side wall of the base structure 1, located in the plane of the paper, and the detector modules 3. Spacer elements 21 may, for example, be sleeves which are slipped over the guide elements. Sleeves of this type, also, for example, produced from aluminum, steel or Invar, may be manufactured with length tolerances of <2 µm and therefore allow very precise positioning of the detector modules 3. Owing to spacer elements 21 of different lengths, the detector modules can be arranged such that the total detector face shown is formed. During assembly, a side wall of the base structure 1 is first removed. The various spacer elements 21 are then slipped onto the guide elements 2 and the detector modules are then slipped on. Clamping elements 22 are used to fix the detector modules 3 in the slipped-on position. These clamping elements 21 may be short sleeves, for example, which have an additional screw guided in the internal thread (indicated in FIG. 4 in the clamping elements 22 as a laterally projecting element), in order to fix the clamping element 22 on the guide element 2. So that the precisely produced guide element 2 is not damaged while it is being fixed, the screw may act, for example, on a rubber mat which then presses against the guide element 2 and thus fastens the clamping element 22. Instead of an external clamping element 22, as shown here, the clamping elements 22 may also be an integral component of a detector module 3 which then, for example, also has a screw, which acts on a rubber mat and thus fixes the detector module on a guide element 2. Other embodiments of clamping elements known to the person skilled in the art, such as, for example, clamping by means of a cone, wherein the surfaces are not damaged, should also be taken into account. Once the spacer sleeves 21, detector modules 3 and clamping elements 22 have been slipped on, the lower side wall is fastened again.

It is also possible to insert spacer elements 21 between the detector modules 3. A detector module 3 should preferably not abut with its sensitive surface against another module, as the sensitive surface can thus be damaged. The detector modules are therefore constructed such that the sensitive surfaces are to be arranged with respect to one another with a certain gap (adapted to the various tolerances to be taken into account). Positioning can thus take place owing to precise spacer elements 21, which are slipped onto the guide elements 2 between the detector modules, so that a gap is ensured between the sensitive surfaces of the detector modules. Positioning by means of spacer elements 21 saves time in the production of a detector and in the process ensures great precision.

FIG. 5 shows a detector according to the invention in a lateral view in the direction of viewing of the extension direction of the guide elements 2. The base structure in this case consists of a rectangular frame (the side walls in the extension direction of the guide elements are indicated by dashed lines) and a base plate. The detector modules 3 which have a sensitive surface 32 and a base body 33 and continuous recesses 31 in the extension direction of the guide elements, are arranged only on one guide element 2 in the embodiment shown. The guide structure 4 in this case is a hole guide worked into the detector base body 33 in the extension direction of the guide elements 2. As the weights of the individual detector modules 3 can lead to the fact that the guide elements 2, which in this embodiment are only held respectively at their ends, bending, a support element 11 is used here which may be a screw guided in an internal thread, for example. Pressure can be applied against a detector module 3 by a support element 11 such that bending is counteracted. In another embodiment, the support can be provided by the base plate itself, in that the detector modules 3 are positioned on the base plate so as to slide.

A side view of an embodiment of a detector according to the invention in the extension direction of the guide elements 2 is also shown in FIG. 6. In this embodiment, the guide elements 2 are profiled rods, which have a round head and a rectangular base, the width of which is smaller than the diameter of the round head. Profiled rods of this type can be arranged in the base plate, for example in that they are guided in corresponding grooves and are adhesively bonded or welded there. Similarly to the embodiment shown in FIG. 1a and 1b, the detector modules 3 have guide structures 4 which are arranged on each side of the detector modules 3, which extend in the extension direction of the guide elements 2 and are used for positioning the detector modules 3 on the guide elements 2. The detector modules 3 have sensitive surfaces 32 and recesses 31.

FIG. 7 shows an embodiment of a detector according to the invention in plan view, which is particularly easy to enlarge. In this embodiment, the base structure consists of side cheeks 1''' and two base plates 1' and 1''. Starting from an original detector with a base plate 1' which is configured such that two detector modules 3 can be positioned in the extension direction of the guide elements 2' the detector can easily be enlarged, in that a second base plate 1'' with guide elements 2'' is joined on. The base plate 1'' can thus for example be fastened by end side cheeks which are adapted with respect to size (in the plane of the paper, side cheeks 1''' terminating the detector to the left and right), while in the original detector with only one base plate 1', the end side cheeks shown are to be imagined replaced by corresponding shorter end side cheeks. The guide elements 2', 2'' may be produced here, as shown in FIG. 6, by profiled rods which are connected to the respective base plate. Guide elements 2' and 2'' respectively arranged one behind the other can be regarded as a continuous guide element 2. A detector can be economically enlarged in this way. The size of the detector can be adapted to the circumstances (for example extension to larger examination volumes). The base plates 1' and 1'' can be provided here with guide structures, for example precision holes and precision pins, so the enlargement can take place with minimal tolerance.

FIG. 8 shows a further embodiment of a detector according to the invention. Guide elements 2 are fastened to a base structure 1 (the terminating side cheek here is not shown to clarify the arrangement, so the visible ends of the guide elements 2 are to be imagined as held in corresponding guide holes in the side cheek, not shown). The detector modules 3', 3'', 3''', 3'''' all have, in this instance, a different surface shape, so ultimately a total detector surface results which is curved corresponding to a cut-out of a spherical surface. The detector module 3' is located centrally in the detector shown and has a planar surface which is located parallel to the x-y plane in the coordinate system shown. The detector module 3'' has a surface which drops in the negative x-direction, so that the height of the detector module 3'' measured in the z-direction is greater at the detector edge than on the side pointing to the detector center. The detector module 3''' has a surface that drops in the negative y-direction, so that the height of the detector module 3''' measured in the z-direction is greater at the detector edge than on the side pointing to the detector center. The detector module 3'''' has a surface that drops both in the negative x-direction and in the negative y-direction, so that the height of the detector module 3'''' measured in the z-direction is greatest at the detector corner and is lowest at the corner which points in the direction of the detector center. Overall, owing to the different detector module designs, a detector surface is produced, which is spherically curved. The sensitive surface of the respective detective modules can be designed here to be planar or curved.

The invention claimed is:

1. A detector comprising a base structure with guide elements,
   detector modules with at least one respective guide structure for positioning relative to at least one of the respective guide elements, wherein
   the guide elements extend in a first direction,
   at least two of the detector modules are positioned consecutively on one of the same guide elements in the first direction and
   there are guide elements which are separated from one another in a second direction.

2. A detector as claimed in claim 1, wherein at least two of the detector modules in the second direction are arranged consecutively on at least two of the guide elements.

3. A detector as claimed in claim 1, wherein at least one spacer element is arranged on at least one of the guide elements between the base structure and one of the detector modules or between two of the detector modules.

4. A detector as claimed in claim 1, wherein the guide elements in the second direction are arranged next to one another with a spacing pattern and the extent of the detector modules in the second direction substantially equals a spacing between two of the guide elements.

5. A detector as claimed in claim 1, wherein the base structure is curved in the second direction.

6. A detector as claimed in claim 1, wherein at least two of the detector elements have a different shape.

7. A detector as claimed in claim 1, wherein the guide elements are rods.

8. A detector as claimed in claim 1, wherein at least one clamping element is provided for fixing one of the detector modules.

9. A detector according to claim 1, wherein the detector modules each have at least one respective continuous recess in the first direction.

10. An X-ray device incorporating the detector as claimed in claim 1.

11. Method for manufacturing a detector, in particular for use in an X-ray device, in which detector modules are slipped each on at least one guide element by means of at least one respective guide structure of the respective detector module, whereby the guide elements extend in a first direction of a base structure and wherein at least two of the detector modules being consecutively slipped onto one of the same guide elements and there are detector modules that are separated from one another in a second direction.

12. The method of claim 11, comprising arranging at least two of the detector modules in the second direction consecutively on at least two of the guide elements.

13. The method of claim 11, comprising arranging at least one spacer element on at least one of the guide elements between the base structure and one of the detector modules or between two of the detector modules.

14. The method of claim 11, comprising arranging the guide elements in the second direction next to one another with a spacing pattern and the extent of the detector modules in the second direction substantially equals a spacing between two of the guide elements.

15. The method of claim 11, comprising curving the base structure in the second direction.

16. The method of claim 11, comprising shaping at least two of the detector elements differently.

17. The method of claim 11, comprising selecting the guide elements are rods.

18. The method of claim 11, comprising fixing one of the detector modules with at least one clamping element.

19. The method of claim 11, forming at least one respective continuous recess in the first direction in each of the detector modules.

20. The method of claim 11, comprising using an X-ray device with the detector.

* * * * *